US011173121B2

(12) United States Patent
Wilhelm et al.

(10) Patent No.: US 11,173,121 B2
(45) Date of Patent: Nov. 16, 2021

(54) PELLETS HAVING A MULTI-LAYER STRUCTURE FOR DELAYED RELEASE OF THE ACTIVE SUBSTANCE IN THE DISTAL COLON

(71) Applicant: Dr. Falk Pharma GmbH, Freiburg (DE)

(72) Inventors: Rudolf Wilhelm, Bischweier (DE); Markus Proels, Freiburg/Breisgau (DE); Roland Greinwald, Kenzingen (DE); Tanju Nacak, Gottenheim (DE); Ansgar Boegershausen, Freiburg (DE)

(73) Assignee: Dr. Falk Pharma GmbH, Freiburg (DE)

( * ) Notice: Subject to any disclaimer, the term of this patent is extended or adjusted under 35 U.S.C. 154(b) by 0 days.

(21) Appl. No.: 17/263,710

(22) PCT Filed: Aug. 22, 2019

(86) PCT No.: PCT/EP2019/072429
§ 371 (c)(1),
(2) Date: Jan. 27, 2021

(87) PCT Pub. No.: WO2020/039017
PCT Pub. Date: Feb. 27, 2020

(65) Prior Publication Data
US 2021/0228487 A1 Jul. 29, 2021

(30) Foreign Application Priority Data

Aug. 24, 2018 (EP) .................................... 18190638

(51) Int. Cl.
*A61K 9/16* (2006.01)
*A61K 9/00* (2006.01)
(Continued)

(52) U.S. Cl.
CPC ............ *A61K 9/1676* (2013.01); *A61K 9/009* (2013.01); *A61K 9/0053* (2013.01);
(Continued)

(58) Field of Classification Search
None
See application file for complete search history.

(56) References Cited

U.S. PATENT DOCUMENTS 5,643,602 A 7/1997 Ulmius

FOREIGN PATENT DOCUMENTS

CN 101108171 * 1/2008 .............. A61P 37/08
DE 43 32 394 A1 3/1995
(Continued)

*Primary Examiner* — Aradhana Sasan
(74) *Attorney, Agent, or Firm* — Smith Patent, LLC; Chatin A. Smith

(57) ABSTRACT

An optimized pharmaceutical formulation for the treatment of inflammatory diseases of the colon is disclosed, wherein the pharmaceutical formulation is a capsule containing pellets, which capsule is suitable for oral administration and delivers the active substance in a targeted manner to the site of action, namely the colon. This is achieved by a complex and multiple coating of pellets, which permit a modified release of active substance. The release of the active substance is at its maximum only in the colon, with at the same time low blood plasma levels. The results of the pharmaceutical tests concerning in vitro release are corroborated by the results in pharmaco-kinetic and clinical studies and the clinical efficacy demonstrated by these. The formulation according to the invention has a very good medicinal safety.

15 Claims, 9 Drawing Sheets

(51) Int. Cl.
*A61K 9/48* (2006.01)
*A61K 9/50* (2006.01)
*A61K 31/58* (2006.01)

(52) U.S. Cl.
CPC .......... *A61K 9/1635* (2013.01); *A61K 9/4825* (2013.01); *A61K 9/5026* (2013.01); *A61K 31/58* (2013.01)

(56) References Cited

FOREIGN PATENT DOCUMENTS

| | | |
|---|---|---|
| DE | 43 40 057 A1 | 6/1995 |
| EP | 1 607 087 A1 | 12/2005 |
| EP | 2 143 424 A1 | 1/2010 |
| WO | WO 2003/080032 A2 | 10/2003 |
| WO | WO 2004/039357 A1 | 5/2004 |
| WO | WO 2017/042835 A1 | 3/2017 |

* cited by examiner

US 11,173,121 B2

PELLETS HAVING A MULTI-LAYER STRUCTURE FOR DELAYED RELEASE OF THE ACTIVE SUBSTANCE IN THE DISTAL COLON

PRIORITY

This application corresponds to the U.S. National phase of International Application No. PCT/EP2019/072429, filed Aug. 22, 2019, which, in turn, claims priority to European Patent Application No. 18190638.9 filed Aug. 24, 2018, the contents of which are incorporated by reference herein in their entirety.

TECHNICAL FIELD OF THE PRESENT INVENTION

For the treatment of inflammatory processes and alterations in the distal colon, such as for example ulcerative colitis, there is needed a dosage form that permits local availability of the active substance budesonide in a sufficiently high concentration at the site of inflammation after oral application. Said concept also referred to as colon targeting cannot be realized with the oral application of a conventional pharmaceutical formulation, since there is a high risk that the active substance cannot be made available in effective concentrations at the site of action, the pathologically altered areas of the colon. Thus, the aim of the colon targeting preferably is to be achieved in that the active substance is released from the formulation with a modified release kinetics in the colon as completely as possible and can be effective there. The present invention is especially suitable to provide a dosage form that can simply and reliably be used and meets said requirements.

BACKGROUND OF THE PRESENT INVENTION

Various formulations for the treatment of inflammatory bowel diseases have been described in the state of the art. There are various manifestations of inflammatory bowel diseases, wherein the Crohn's disease can manifest in the different areas of the intestine. There are manifestations in which a main emphasis of the inflammatory areas is in the duodenum. With other forms it is in the jejunum or ileum or also in the large intestine. In some patients, the affected areas extend over wide parts of the intestine. On the other hand, ulcerative colitis almost exclusively manifests in the large intestine, wherein also the large intestine is divided into different areas. In most cases the rectum is involved from which the disease progresses into the sigmoid colon and colon.

It is a challenge for the pharmaceutical technology to provide the active substance as exactly as possible at the site of the intestine at which the active substance is needed. Said problem, to release the active substance quite predominantly in the colon, is not satisfactorily solved by formulations known in the state of the art.

In WO 91/07172 compositions for the treatment of inflammatory bowel diseases are described that can be administered orally, wherein one of the active substances is budesonide. The pellets described there are constructed such that a layer of the active substance is applied to starter cores, wherein this is coated with two different layers that are sprayed onto the carrier pellets with the active substance layer. In WO 95/08323 there are disclosed budesonide pellets having a controlled release pattern. These pellets from the inside to the outside contain neutral pellets, an active substance layer, an inner lacquer layer of enteric juice-soluble lacquers, and an outer lacquer layer of gastric juice-insoluble, enteric juice-soluble lacquers. The thereby achievable release of the active substance after passage of the stomach cannot satisfactorily be used for the described indication (ulcerative colitis). The desired delayed continuous release of the active substance in the colon is not achieved. The pellets containing hard capsules described in the state of the art have an early, prompt and fast release which results in the fact that only little active substance reaches the colon at all.

Pharmaceutical formulations having multiple coatings are also disclosed in WO 03/045356 or WO 2017/216088, wherein also mucoadhesive materials are provided. Further formulations for controlled release are disclosed in WO 2009/138716 or in WO 00/76478, wherein the active substances are partially incorporated into three-dimensional matrices, whereby a delayed release is effected. Also known are complex drug formulations continuously releasing the active substance from a matrix (Cortiment-MMX retard tablets). WO 02/17887 discloses drugs for the treatment of bowel diseases, wherein the active substance is mainly released into the distal segments of the intestine. These are pellets, granules, mini-tablets preferably containing 5-amino salicyclic acid and are individually coated with an enteric lacquer and with a second lacquer.

In EP 2 143 424 there are disclosed pharmaceutical forms for the colon-specific administration. The composition comprises a core coated with a layer having the active substance. Applied thereon is an intermediate layer of cationic polymer that is swellable at a pH value of not more than 6.6 and an outer layer that is an anionic polymer that is soluble at a pH of not less than 7.0. The release of the active substance after a delay of about 300 minutes takes place relatively fast, sudden, and complete.

DE 43 32 394 describes budesonide pellets having a controlled release profile, wherein the neutral pellets have an active substance layer of budesonide and excipients and comprise two different lacquer layers.

WO 03/080032 describes pharmaceutical formulations substantially comprising a core with the active substance budesonide, a middle layer with an intestinal-juice soluble polymeric coating agent, and an outer enteric coating.

EP 1 607 087 discloses oral formulations for the administration to the colon.

Gross et al., Journal of Crohn's and Colitis (2011) 5, 129-138 report a study in which it turned out that treatment with 3 g of mesalazine granules (Salofalk®) provides better results than a treatment with 9 mg of orally administered budesonide, because with the budesonide preparations known from the prior art the release in the colon could not reliably be ensured.

The pharmaceutical formulations known from the prior art have in common that the desired release of the active substance budesonide is not ensured such that the active substance is almost completely provided at the inflamed areas in the entire large intestine, and in particular also in the rectum.

SUMMARY OF THE PRESENT INVENTION

The object of the present invention are pellets for the delayed and continuous release of the active substance in the entire colon (FIG. 1) having a multi-layer coating, wherein the pellet has the following components (FIG. 2):

a) a starter pellet only consisting of an inert material and having no pharmaceutically active substance inside the starter pellet, b) an active substance layer that is directly applied to the starter pellet and in addition to the active substance only contains excipients conventional in pharmaceutics, c) a swelling layer that is directly applied to the active substance layer and contains swelling materials that swell upon contact with intestinal fluid, d) a retard layer that is also not soluble in intestinal fluid at a pH value >6.5, but becomes permeable for fluids, and is directly applied to the swelling layer, e) an outermost coating that does not dissolve at a pH value <5.5, but well dissolves at a pH value greater than 6.0.

In a preferred embodiment there are no further intermediate layers between the individual layers, as stated above. That is that the active substance layer (b) is directly applied to the starter pellet (a) and that a swelling layer (c) is directly applied to the active substance layer.

A coating (d) that is a retard layer is directly applied to the swelling layer and the outermost coating (e) that is enteric is directly applied thereto.

BRIEF DESCRIPTION OF THE FIGURES

Essential aspects of the present invention are shown and explained in the attached figures:

FIG. 5 proves that a retard layer without an underlying swelling layer does not allow a release of the active substance.

FIG. 7 proves that by means of the formulations according to the invention indeed the entire colon can effectively be treated. In Example 6, efficacy and tolerance of the budesonide pellets according to the invention have been investigated, wherein FIG. 7 shows the proportion of the patients with clinical remission depending on the localization of the respective disease.

FIG. 8 proves that the number of the hemorrhagic feces per week could effectively be decreased in the course of the treatment time.

DETAILED DESCRIPTION OF THE PREFERRED EMBODIMENTS

Figure 1:
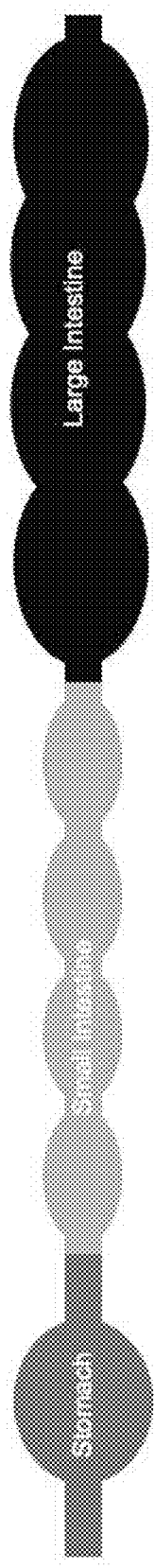
FIG. 1 represents a schematic of the digestive tract.

The present invention relates to a pharmaceutical formulation that comprises budesonide as the effective component or a pharmaceutically acceptable salt thereof and that is preferably used for the treatment of inflammatory diseases of the colon.

The starter pellets (a) used have an average diameter of 0.2 to 2.0 mm, wherein at least 90% of the particles lie within the given size range. Moreover, the starter pellets have a spherical shape of uniform surface condition.

Pharmaceutical pellets are powder particles of a nearly spherical shape with an average diameter of 0.2 to 2 mm, uniform surface, and narrow particle size distribution. The surface is smooth and of low porosity.

It is important that the beads used as the starter pellet meet certain qualitative requirements. A possible pellet material are sugar pellets consisting of sucrose and corn starch, wherein the sucrose content should not be higher than 90 wt %. Preferably, the pellets have a narrow range of the particle size distribution, because this is one of the requirements for a homogeneous distribution of the finished pellets. The particles have a diameter between 0.2 and 2.0 mm, preferably 0.7 to 1.4 mm, wherein a range between 0.85 and 1.0 mm is particularly preferred. When preparing the pellets care must be taken that the size distribution is within a relatively narrow range, so that for example at least 90%, preferably at least 95% of the particles are in the given range. The methods for determining the particle size and for determining the distribution of the particle size are described in the European Pharmacopoeia. In this regard we refer to chapter 2.9.38.

Another essential aspect concerns the surface condition. The starter pellets should correspond to an ideal sphere as good as possible, wherein the surface shall be as smooth as possible and without recesses or protruding projections. For example, the quality of the pellets can be monitored by means of a stereomicroscope and a digital camera coupled thereto. The pictures may be evaluated by means of a suitable software.

According to the invention the topically effective corticosteroid budesonide is used as the active substance. Budesonide is hardly water-soluble. Therefore, in a preferred embodiment micronized budesonide is used.

Especially suitable for the application is the use of micronized budesonide (specification of the particle diameter distribution: 100%<10 µm and ≥95%<5 µm; determination method: laser diffraction). The physical-chemical properties of budesonide are known (literature: e.g. Merck Index, comment to Pharmacopoeia):

White to almost white crystalline powder

The solubility in aqueous systems is virtually pH independent and is 0.014 mg/ml.

Specific Rotation $[\alpha]^D_{20}$ of epimer A is +98.9 (0.28%; in dichloromethane)

pKa value: 12.85±0.10

Melting Point: 221° C.-232° C.

When selecting the form of administration according to the invention it is assumed that the continuous release is from the intact dosage form and that the passage and transit times in the gastro-intestinal tract will not adversely be affected (e.g., by longer retention times in the stomach after food intake). The dose of the medicinally effective component can be distributed over a generally homogeneous, but large outer surface and flexibly adjusted. Said properties are achieved with the multi-particular form of administration, namely the pellets, according to the invention. Here, filling of a defined amount of pellets into hard capsules or portion packages such as e.g., stick packs, permits adjustment, administration and application of a defined dose of budesonide. The properties of the drug formulation described in the particularly preferred embodiment allow the variable single-dosage administration of budesonide in an amount of 3 to 9 mg.

The application of the budesonide-containing drug formulation according to the invention significantly reduces the risk of an undesired intake of budesonide into the systemic circulation. The multi-particular form of administration is of advantage over the "single-unit" formulations described in the prior art in that the active substance is released reproducible and robust, that is less variable, over a large area of the inflamed colon and thus, is particularly suitable for the treatment of the intestinal segments affected by an inflammation. In this way, the budesonide dose to be administered can be distributed over a large surface, wherein said surface is located in the area of the colon.

An early release of the medicinally effective component from the form of administration according to the invention in the stomach is avoided by resistance of the outermost coating (e) to gastric juice. Due to said enteric outermost coating (e) the outermost coating of the pellets is not dissolved in the stomach. The stomach has a pH value of about 1 to at most about pH 5. As long as the pellets are in the area of the stomach, the outermost coating layer does not dissolve. Only after the passage into the small intestine the pH value is increased and the outermost coating (e) dissolves. In the small intestine and depending on the time, intestinal fluid penetrates through the layer next to the outermost coating layer (d) into the interior of the pellets. The retard layer (d) does not dissolve upon contact with the intestinal fluid. However, due to its permeability the fluid contacts the underlying swelling layer (c). By the fluid contact the swelling layer (c) starts to swell and to increase its volume. As a result, the pressure inside the pellets and to the retard layer increases. Said pressure leads to the fact that openings or defects are formed in the retard layer through which dissolved budesonide can diffuse from the innermost active substance layer (a) to the outside. In the further passage of the pellets through the lower digestive tract said process is continuously continued so that finally a complete budesonide release from the pellets through the thus opened retard layer becomes possible.

The start of the release only takes place at a pH value of >6 with a short delay time. Subsequently, the active substance is continuously and pH-independently released over a period of ca. 9 hours so that at the end an almost complete release of budesonide from the pellets has taken place, what corresponds to an amount of more than 85% of the declared amount of active substance. Here it is essential that the release of the active substance does not take place suddenly or in a short time interval of 1 to 2 hours, but more or less uniformly in a period of about 8-10 hours, preferably of 9 hours.

The release of the active substance budesonide from pellets according to the present invention is determined in the examples by the following in vitro release:
   test equipment: blade stirrer equipment (equipment 2 of the European Pharmacopoeia)
   stirring rate: 75 revolutions/minute
   test media:
      (a) artificial gastric juice: (simulated gastric fluid, SGF)
         medium: 0.1 N HCl, pH 1, 0.1% polysorbate 80
         volume: 900 ml
            test time: 2 hours
         criterion: gastric juice resistance (no release)
      (b) artificial intestinal juice: (simulated intestinal fluid, SIF)
         medium: phosphate buffer with 0.1% polysorbate 80 and an osmolality of approx.
         270 mOsmol/kg as well as a pH value of 6.5.
         volume: 900 ml
         test time: 16 hours
         criterion: complete release In the individual measurement experiments, first the pellets have been left in artificial gastric juice for two hours. Since here a pH value of 1.2 has been set, lacking release of the active substance budesonide shows intactness of the pellets. After two hours the pellets were taken out and transferred into artificial intestinal juice having a pH value of 6.5. The release of the budesonide into the medium was measured. The pellets according to the invention are characterized in that during the first two hours (in artificial gastric juice) virtually no budesonide was released. After two hours (in artificial intestinal juice) a continuous release of budesonide started that allowed a "colon targeting".

When testing formulations known from the prior art a release of budesonide has been observed partially already in the gastric juice. On the other hand, also in the intestinal juice a fast release has just been observed in the first hours. Such a release profile is not useful for the intended purpose, because the release of the budesonide primarily takes place in the small intestine and possibly in the initial areas of the large intestine, but not—such as desired—primarily in the colon.

For the preparation of pharmaceutical pellets there are primarily described two different production methods: Coating starter cores (multilayer pellets) as well as wet and melt extrusion. Multilayer pellets (according to the invention) are multi-coated starter pellets, wherein the starter cores are active substance-loaded sugar-starch pellets (so called Nonpareille), for example. Here, the active substance first is sprayed onto the surface of the Nonpareilles as an own layer before further functional layers are applied that modify the release of the active substance. Here the single layers are continuously applied or sprayed in the fluid bed so that the pellets get their specific functionality.

Figure 9:
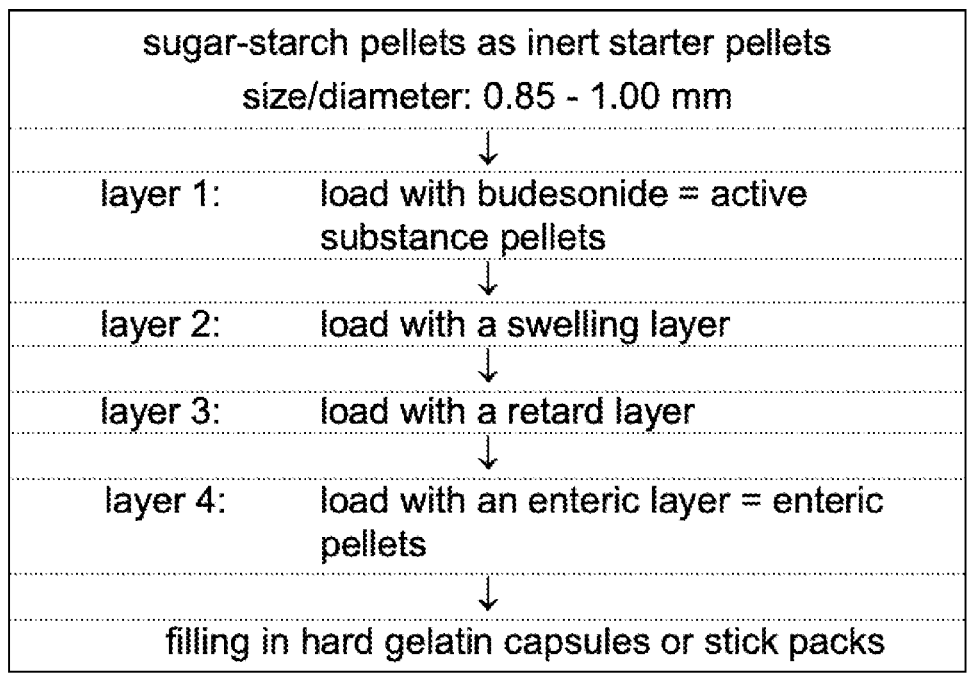
FIG. 9 presents a scheme for the build-up of the developed multilayer pellets of the present invention.

According to the invention, multilayer pellets are used for colon targeting of budesonide. The scheme contemplated for the build-up of such developed multilayer pellets is presented in FIG. 9.

Surprisingly it could be shown that it is only the complex and systematic build-up of the pellets according to the invention via starter pellets, active substance pellets, swelling layer pellets, retard pellets, and enteric pellets that is suited to ensure the transport to the colon as well as the subsequent continuous release of the budesonide in the colon.

In addition to said stringent structural build-up of the multilayer pellets the selection of suitable excipients for the individual layers is a further crucial feature of the application according to the invention. Only by the interaction of structure and composition it is possible to optimally take advantage of the multi-particular form of administration for the active substance budesonide considering the required colon targeting.

The individual layers of the preferred pellets according to the invention beginning with the starter cores have the following qualitative composition:

Active substance pellets

The active substance budesonide is applied onto the starter pellets (sugar-starch pellets) in an organic-aqueous suspension consisting of water and isopropyl alcohol (mass ratio of 80% w/w and 20% w/w) as well as the further components lactose monohydrate (function: filler), polyvinylpyrrolidone (PVP) of the Kollidon® K25 type (function: binder), polyoxyethylene (20) sorbitane monooleate (Polysorbate® 80; Tween 80) (function: wetting agent), and talcum (function: separator). The solids content of the suspension is ca. 27% w/w. After loading and drying the pellets budesonide adheres to the starter pellets.

Swelling layer pellets:

Subsequently, the active substance pellets are sprayed with an alcoholic suspension of homopolymeric, cross-linked polyacrylic acid of type A (carbomer; viscosity [0.5%]=4000-11000 mPas; approx. relative molar mass: 1250000) (function: swelling agent), polyvinylpyrrolidone (PVP) of the Kollidon® K25 type (function: binder), and talcum (function: separator). In this way, loading with the swelling layer takes place. Here, isopropyl alcohol is used as the solvent. The solids content in the suspension is ca. 11% w/w.

Retard layer pellets:

In the next step, the pellets are film-coated with the polymer combination modifying the active substance release. Here, a combination of ammonium methacrylate copolymer type B (poly(meth)acrylic acid methyl/ethyl/2-trimethyl aminoethylester copolymer with a ratio of ethyl acrylate to methyl methacrylate and trimethyl ammonium ethyl methacrylate of 1:2:0.1=Eudragit® RS 12,5) and ammonium methacrylate copolymer type A (poly(meth)acrylic acid methyl/ethyl/2-trimethyl aminoethylester copolymer with a ratio of ethyl acrylate to methyl methacrylate and trimethyl ammonium ethyl methacrylate of 1:2:0.2=Eudragit® RL 12,5) is used. Both polymers form water-insoluble, but permeable films, that are added in a 12.5% w/w solution in isopropyl alcohol (60% w/w) and acetone (40% w/w) with sodium lauryl sulphate as a wetting agent of the spraying solution or suspension, respectively. The spraying solution or suspension, respectively additionally also contains triethyl citrate (function: plasticizer) and talcum (function: separator). The solids content of the organic-aqueous spraying solution or suspension, respectively is ca. 14% w/w. The components of the retard layer are suspended in said spraying solution or suspension, respectively that consists of isopropyl alcohol (ca. 88% w/w) and water (ca. 12% w/w). After film-coating and drying of the pellets the retard layer directly lies on the swelling layer.

Enteric pellets:

In the last step the pellets are enterically coated. For that, an organic-aqueous solution of Eudragit® L (polymethacrylic acid/polymethylmethacrylate copolymer with a ratio of polymethacrylic acid to polymethylmethacrylate of 1:1) is used. The polymer forms an intestinal juice-soluble coat. In addition to the anionic polymer the spraying solution or suspension, respectively also contains triethyl citrate (function: plasticizer) and talcum (function: separator) so that a solids content of ca. 15% is obtained. The solvent consists of 85% w/w of isopropyl alcohol and 15% w/w water. Loading the pellets with said layer ensures that no release of active substance in the stomach takes place.

Preferably, coating of the pellets with the individual layers takes place in fluid bed plants. Since the individual layers are applied as liquids or suspensions, respectively the liquid phase used as a carrier has to be removed. This is done by a suitable ventilation, wherein the ambient temperature can moderately be increased, however only up to such a temperature that no undesired side-reactions take place.

The desired functionality of the multilayer pellets results from the optimal, sequential dissolution and swelling of the applied layers on the way through the digestive tract: as soon as the pellets reach the small intestine first the polymer of the outermost layer (e) dissolves. The intestinal digestive fluid penetrates the permeable retard layer (d) into the interior of the pellets. The pH ratios of the small intestine (pH<5.5-ca. 7.2) result in swelling of the polyacrylic acid, the polymer of the swelling layer. The associated increase in volume increases the internal pressure to the retard layer, whereby continuous defects are formed in said layer. In this way, openings are formed through which the budesonide dissolved in the digestive fluid can diffuse to the outside. In this way, the active substance dissolved in the digestive fluid can diffuse to the outside over a long period and so be released at the site of action and act locally. Said process runs time-dependent and starts to the full extent when the pellets have reached the colon.

A dose of the so developed multilayer pellets can be filled into hard gelatin capsules. The qualitative and quantitative composition of a preferred capsule at a dose of 9 mg of budesonide is summarized in Table 1. Here, the solvents used are not part of the composition, since they are dried out as volatile components during the process.

Various prototypes of the preferred embodiment have been prepared that essentially have a combination as illustrated in detail in Table 1.

TABLE 1

Composition of preferred budesonide multilayer pellets according to the invention in one capsule
Composition [mg]

| Component | Function | Amount per Capsule |
|---|---|---|
| 1. Active substance pellets | | |
| budesonide | medicinally effective component | 9.00 mg |
| lactose monohydrate | filler | 36.00 mg |
| polyvinylpyrrolidone (Kollidon ® K25) | binder | 2.70 mg |
| polyoxyethylene(20) sorbitan mono-oleate (polysorbate 80; Tween 80) | wetting agent | 0.71 mg |
| talcum | separator | 16.50 mg |
| sugar-starch pellets | starter pellets | 260.00 mg |
| sum: | | 324.91 mg |
| 2. Swelling layer pellets | | |
| carbomer | swelling agent | 24.00 mg |
| polyvinylpyrrolidone (Kollidon ® K25) | binder | 18.00 mg |
| talcum | separator | 18.00 mg |
| sum: | | 384.91 mg |

TABLE 1-continued

Composition of preferred budesonide multilayer pellets according to the invention in one capsule
Composition [mg]

| Component | Function | Amount per Capsule |
|---|---|---|
| 3. Retard layer pellets | | |
| Eudragit ® RS 12, 5 | retard polymer | 6.30 mg |
| Eudragit ® RL 12, 5 | retard polymer | 2.70 mg |
| triethyl citrate | plasticizer | 0.90 mg |
| talcum | separator | 7.20 mg |
| sum: | | 402.01 mg |
| 4. Enteric Pellets | | |
| Eudragit ® L | intestinal juice-soluble polymer | 16.00 mg |
| triethyl citrate | plasticizer | 1.60 mg |
| talcum | anti-sticking agent | 8.00 mg |
| sum: | | 428.81 mg |
| 5. Hard gelatin capsule | | |
| gelatin with titania | capsule shell | 97.00 mg |
| total: | | 525.81 mg |

The in vitro release profile of the pellets according to the invention is given in Example 1. The required criteria of gastric juice resistance and continuous release in the artificial intestinal juice are met in accordance with the specifications. Example 2 shows that the desired release of budesonide from the pellets can surprisingly be realized only by the combined use of the swelling and retard layer. Only the sequential coating of the swelling and retard layer described for the application according to the invention to the active substance pellets makes it possible to pass budesonide to the site of action in the colon.

Negative Example (extrusion pellet, Example 4)

It was tried to develop a pharmaceutical formulation showing the desired release profile, with a technology variant via extrusion with subsequent spheronization.

Extrusion pellets (negative example) are powder agglomerates, wherein the preparation of the particles is done by wet or melt extrusion of a powder mass with subsequent spheronization. Extrusion pellets were only used as a reference. Generally, extrusion pellets permit a higher active substance load than multilayer pellets, which however in the present invention is not relevant, since topic corticoids are administered in low doses. For extrusion, screw extruders are used, wherein by applying pressure a wet or molten mass can be pressed through openings of a certain size. The thus obtained strands are cut into cylindrical pellets and subsequently rounded to spheres. The pellets can also be coated in fluid bed plants. In contrast to multilayer pellets extrusion pellets are prepared batchwise. Essentially for the selection of the pellet type are inter alia the physical-chemical properties of the active substance to be processed, the required active substance load, and the desired release mechanism to obtain a targeted release profile. According to the invention no extrusion pellets are used.

Figure 10:
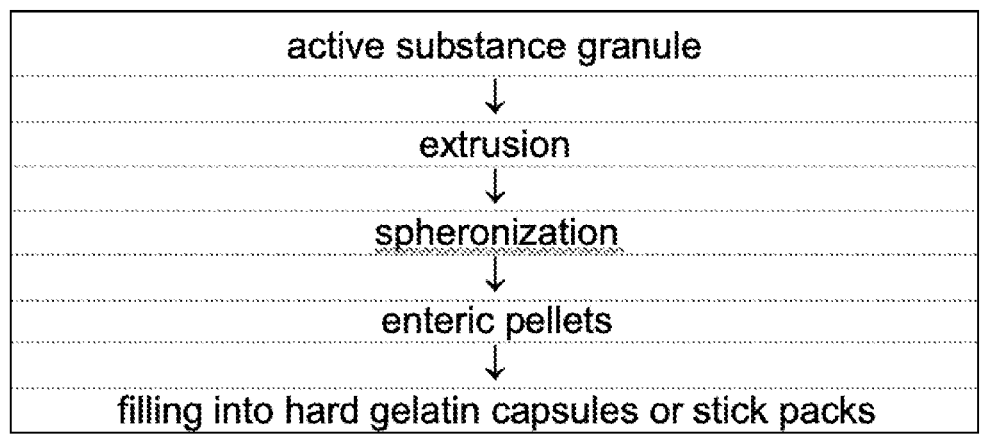
FIG. 10 presents a scheme for the build-up of the extrusion pellets of the present invention.

A scheme for the build-up of the extrusion pellets regarding the qualitative composition and preparation is presented in FIG. 10.

Active substance granule:

A powder mix of budesonide, lactose monohydrate (function: filler), carrageenan (Gelcarin GP911 NF) (function: matrix former and extrusion aid), and calcium chloride (function: enhancement of gel or matrix formation) was water-based granulated. The granulation liquid still contained polyvinyl acetate (Kollicoat SR 30D) (function: retard polymer and matrix former). After having sieved the wet mass there was performed extrusion.

Extrusion and Spheronization:

The wet mass was pressed in a screw extruder at 65° C. through a perforated plate (template having defined opening, Ø1.0-2.2 mm) and subsequently cut to cylindrical molded parts. Said molded parts are rounded off at max. 50° C., dried, and finally the fines are separated by sieving (mesh width: 1000 µm).

Enteric Pellets:

In the last step the rounded pellets are enterically coated. For that, an aqueous suspension of a mixture of Eudragit® FS 30 D (poly(meth)acrylic acid methylester copolymer) and Eudragit® L 30 D 55 (poly(meth)acrylic acid ethylester copolymer) in a ratio of ca. 80% w/w and 20% w/w is used. Both polymers form an intestinal juice-soluble coat. Besides, the aqueous suspension also contains triethyl citrate (function: plasticizer), glycerol monostearate (function: anti-sticking agent), and the wetting agent polyoxyethylene(20) sorbitan mono-oleate (Polysorbate® 80; Tween 80) as well as sodium lauryl sulphate, so that a solids content of ca. 21% is obtained. Loading the extrusion pellets with said layer ensures that there is no release of active substance in the stomach.

A dose of the thus developed extrusion pellets can be filled into hard gelatin capsules. The qualitative and quantitative composition of a capsule with a dose of 9 mg of budesonide is summarized in Table 2. Here, the solvents used are not part of the composition, since they are dried out as volatile components during the process.

The formulation has been developed with the aim that the matrix of the pellets swells by the penetrated digestive liquid after having reached the small intestine and dissolved the polymers of the outermost layer. In this way, there should take place a gradual erosion of the particles during the passage of the intestine segments and thus, result in a continuous active substance release.

The in vivo release profile of the extrusion pellet is given in Example 4. The required criteria for a targeted, topic application in the colon are not met by the extrusion pellets. That is, said approach of development does not lead to the desired "colon targeting".

TABLE 2

Composition of the budesonide extrusion pellets-containing capsule (negative example)
Composition [mg]

| Component | Function | Amount per Capsule |
|---|---|---|
| 1. Active substance granule | | |
| budesonide | medicinally effective component | 9.00 mg |
| polyvinyl acetate (Kollicoat SR 30D) | retard polymer, matrix former | 52.50 mg |
| lactose monohydrate | binder | 28.50 mg |
| carrageenan (Gelcarine GP911 NF) | matrix former, extrusion aid | 240.00 mg |
| calcium chloride | gel and matrix former | 20.00 mg |
| sum: | | 350.00 mg |

TABLE 2-continued

Composition of the budesonide extrusion pellets-containing capsule (negative example)
Composition [mg]

| Component | Function | Amount per Capsule |
|---|---|---|
| 2. Enteric Pellets | | |
| Eudragite ® FS 30 D | intestinal juice-soluble polymer | 48.00 mg |
| Eudragite ® L 30 D 55 | intestinal juice-soluble polymer | 12.00 mg |
| triethyl citrate (Citrofol AL) | plasticizer | 2.80 mg |
| glycerol monostearate | anti-sticking agent | 3.10 mg |
| polyoxyethylene(20) sorbitan mono-oleate (Polysorbate ® 80; Tween 80) | wetting agent | 1.10 mg |
| sum: | | 417.00 mg |
| 3. Hard Gelatin Capsule | | |
| gelatin with titania | capsule shell | 97.00 mg |
| total: | | 514.00 mg |

Figure 3:
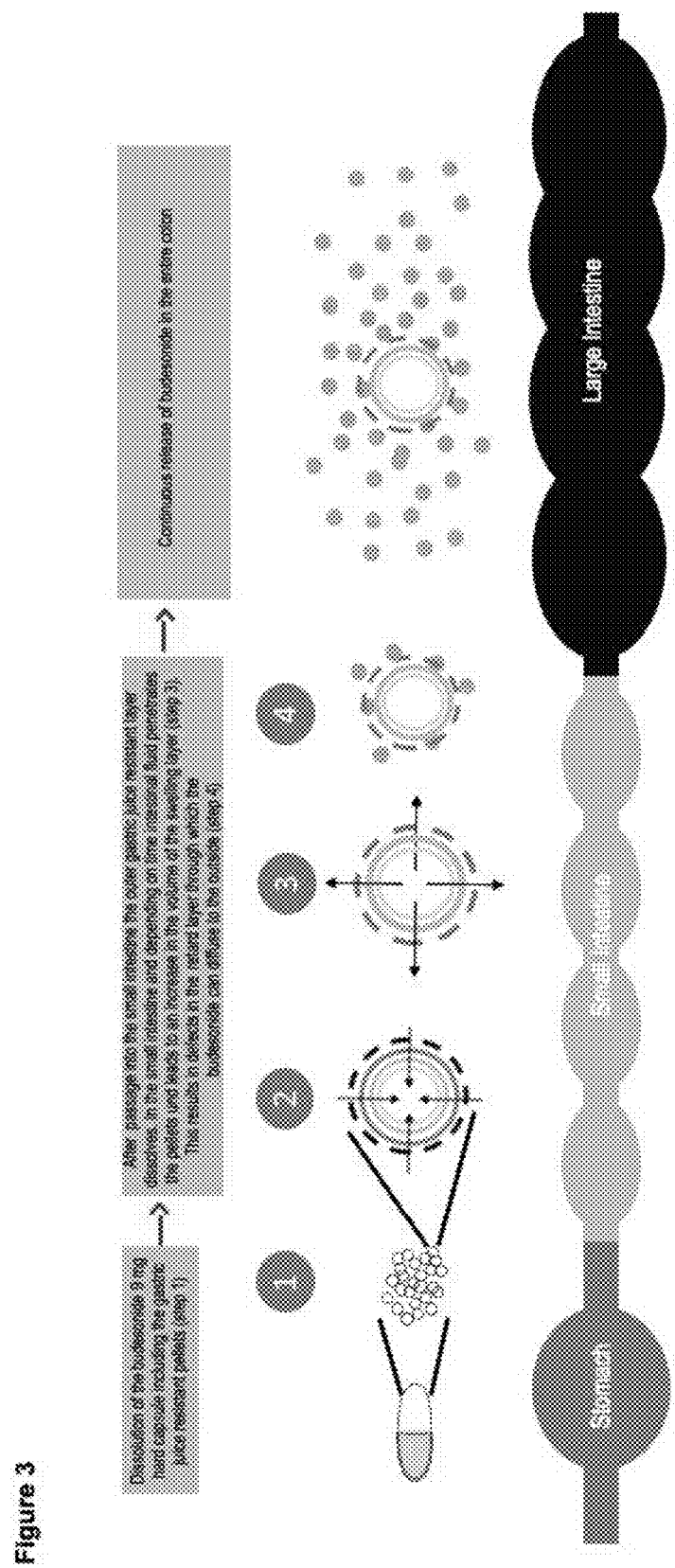
In FIG. 3 there is represented the mode of action of the pellets according to the invention depending on the respective region in the digestive tract.

Dissolution of the formulation according to the invention is schematically illustrated in FIG. 3.

In contrast to the negative comparative example the multilayer pellets according to the invention showed completely different blood levels. Here, after having dissolved the enteric film the already-described complex release mechanism is triggered. The plasma levels of budesonide do not flood, but show a modified, delayed and prolonged course over several hours.

The results of the pharmaco-kinetics study confirm the in vitro results in Example 1 and impressively demonstrate that the active substance is released over the entire passage time of the large intestine from the multilayer pellets and thus, arrives at sites where it can develop its effect on the mucosa of the colon.

In an open, monocentric, randomized pharmaco-kinetics study the multilayer pellets according to the invention were compared to Budenofalk 3 mg hard capsules from the prior art. The average plasma concentrations of the active substance were measured after oral single administration of a dose of 9 mg over time, wherein the bioavailability of budesonide is known from the reference formulation. Example 3 shows the results of the comparative pharmaco-kinetics study.

As can be seen from the plasma levels in Example 3 the formulation described in the prior art is suitable to specifically transport budesonide into the colon. The blood level of budesonide increases fast and strongly. Said course is undesired for colon targeting, since the active substance does not arrive at the site of action in a sufficient concentration, but is already resorbed in advance to large extent in the upper small intestine segments and thus, is no longer available for a local or topic efficacy, respectively in the large intestine. Said in vivo behavior can be explained with the composition of the formulation. The Budenofalk 3 mg hard capsules described in the prior art only contain enterically coated budesonide pellets. After stomach passage said coat dissolves with a certain delay time and then, the active substance is immediately and completely released. In this way, the colon is not reached. The results of a clinical study, in which said formulation described in the prior art has been tested, also show that Budenofalk 3 mg hard capsules (described in WO 95/08323) are not suitable for the treatment of ulcerative colitis. An efficacy in the treatment of patients having a light to moderate ulcerative colitis that can at least be compared to a mesalazine therapy could not be shown (Gross et al., 2011).

Also, efficacy and tolerance of the new multilayer pellets was investigated in an open, clinical study. As described in Example 5 the results impressively prove the clinical efficacy of the pellets. The results demonstrate that the pellets according to the invention bring the active substance to the desired target site and patients who have fallen sick with an ulcerative colitis and could not sufficiently be treated with mesalazine (mesalazine-refractory) can successfully be treated.

In contrast to the multilayer pellets the course of the blood level of the extrusion pellets (negative example) obtained in the pharmaco-kinetics study in Example 4 equals more the prior art than the desired target profile of a formulation releasing in the colon. The budesonide levels even flood even faster than with the reference formulation and also correspondingly fall back faster, so that the active substance release is completed before the colon is reached and obviously, no noteworthy amounts of budesonide reach the large intestine.

EXAMPLES

Various in vivo pharmaco-kinetics profiles have been measured using the above-described materials and methods. The following examples illustrate the invention.

Example 1: In Vitro Release Trials of the Budesonide Multilayer Pellets (Formulation According to the Invention)

To show the effect as well as the impact of the individual layers on the active substance release the in vitro trials have been performed with active substance pellets, swelling layer pellets, retard layer pellets, and enteric pellets from one batch. Here, the test was carried out with an amount of pellets that corresponds to a dose of budesonide of 9 mg. The outer hard gelatin capsule has no influence on the active substance release of the pellets and thus, was omitted in said trials.

Here, the in vitro release trials of the pellets comprised a two-stage test. In the first step the pellets were tested in the artificial gastric juice (pH 1.2) over a period of two hours with subsequent transfer of the test patterns into artificial intestinal juice (pH 6.5) as well as a further test of the active substance release over 7 hours. In order to ensure sedimentation conditions both media contained 0.1% of polysorbate 80 as wetting agent. Here, the parameters of the release test were as follows:

Release Equipment: equipment 2 of the European Pharmacopoeia described in chapter 2.9.3 (stirrer blade method)
Volume of the release medium: 900 ml artificial gastric juice (SGF) 900 ml artificial intestinal juice (SIF)
Speed of Rotation: 75 revolution per minute
Temperature: 37.0° C.±0.5° C.
Test Media:
   Artificial Gastric Juice (SGF): 0.1 N HCl with 0.1% polysorbate 80. pH 1.2
   Artificial Intestinal Juice (SIF): phosphate buffer ($KH_2PO_4$, NaCl, NaOH) with 0.1% polysorbate, pH 6.5

Batch of the Test Patterns: 180013457
Number of Test Patterns: N=6
Sample Pick:
    Active Substance Pellets: 5, 10, 15, 30, 45, 60, and 120 minutes in the artificial gastric juice
    Swelling Layer Pellets: 5, 10, 15, 30, 45, 60, and 120 minutes in the artificial gastric juice as well as
        15, 30, 45, 60, 90, and 180 minutes in the artificial intestinal juice
    Retard Layer Pellets: 15, 30, 45, 60, 90, and 120 minutes in the artificial gastric juice
        30, 90, 150, 210, 270, 330, 390, and 420 minutes in the artificial intestinal juice
    Enteric Pellets: 15, 30, 45, 60, 90, and 120 minutes in the artificial gastric juice
        30, 90, 150, 210, 270, 330, 390, and 420 minutes in the artificial intestinal juice
    Determination of Content of Budesonide: HPLC/UV ($\lambda$=255 nm)

Figure 4:
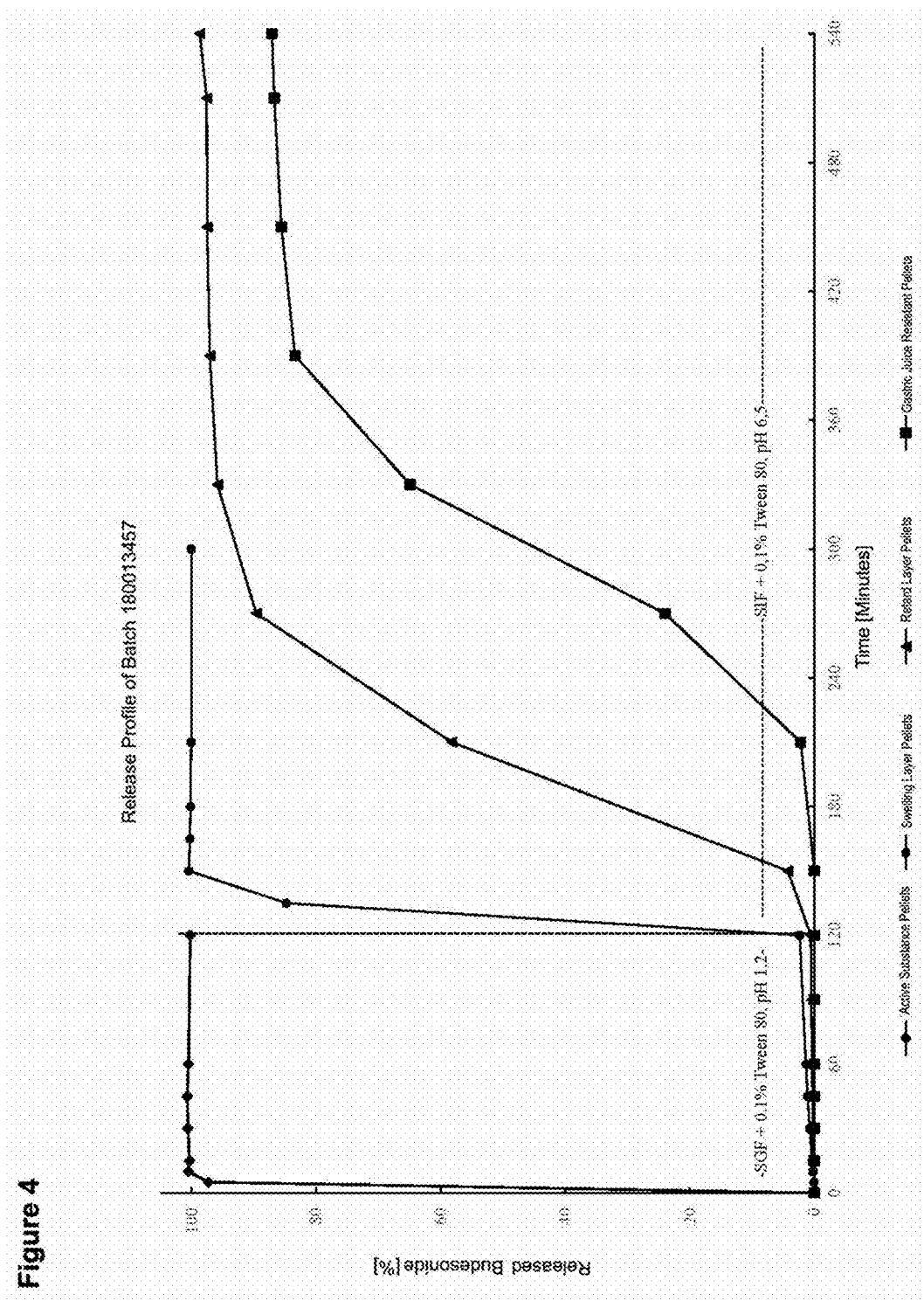
FIG. 4 shows the in vitro release profiles of various pellets, wherein active substance pellets, swelling layer pellets, retard layer pellets, and enteric pellets are compared to each other in view of the release, wherein the formulation according to the invention is designated as enteric pellets. The conditions are explained in detail in Example 1. SGF means artificial gastric juice; SIF means artificial intestinal juice.

FIG. 4 shows the in vitro release profiles of the single pellets. The active substance pellets (without a coating) already completely release in the gastric juice. After 5 minutes more than 85% of the budesonide are dissolved. The swelling layer pellets show a small release within the two-hour test in the gastric juice (<5%) and after transfer in intestinal juice medium completely release within 15 minutes (≥85%). Said behavior reflects the physical-chemical properties of the polyacrylic acid (carbomer) used that is either insoluble, swellable, or soluble due to its pKs value of ca. 6 depending on the pH value of the medium. Under the conditions of artificial gastric juice (pH 1.2) the highly molecular polymer of the acrylic acid is present protonated and is insoluble. The swelling layer remains on the pellets. After transfer into the intestinal juice buffer, the pH value increases into the range of the pKs value and results in a partial deprotonation of the carboxylic acids. That's why water molecules can be incorporated into the narrow polymer skeleton, which results in the build-up of a gel skeleton and thus, to swelling. However, without the retard layer said effect of the swelling layer does not apply and budesonide is rapidly released.

Only after having applied the retard layer onto the swelling layer pellets the above-described effect can fully develop within the pellets (see FIG. 4: release profile of the retard layer pellets). The release profile of the retard layer pellets in the intestinal juice significantly changes and turns into the desired sigma shape associated with a delayed release of budesonide. After ca. 120 minutes in the gastric juice there is achieved the complete active substance release from such retard layer pellets in the intestinal juice after further ca. 150 minutes. Early release in the gastric juice therefore does not occur.

But only the final formulation with an additional enteric coating finally shows the release profile of the formulation according to the invention that is desired for colon targeting. The release of budesonide starts ca. 90 minutes after stomach passage. Early release therefore does not occur. After this time the pellets have passed the small intestine and reached the colon. Subsequently, the active substance is continuously released with a sigmoidal kinetics over at least seven hours. In summary, release of the formulation according to the invention in said in vitro system is based on the following criteria:

SGF ("simulated gastric fluid" corresponding to artificial gastric juice), pH 1.2: after 2 hours: no release=gastric juice resistance SIF ("simulated intestinal fluid" corresponding to artificial intestinal juice), pH 6.5:
    after 270 min.: 10-30% release
    after 330 minutes: 40-70% release
    after 540 minutes: ≥80% release The results of the content determination of the active substance, swelling layer, retard layer and enteric pellets with HPLC/UV prove that the pellets tested in the individual in vitro release investigations were loaded with the required amount of budesonide of 9 mg (corresponding to the contents of one capsule).
    active substance pellets: 100.0%
    swelling layer pellets: 101.9%
    retard layer pellets: 101.6%
    enteric pellets: 100.3%

Example 2: In Vitro Release Trials of Budesonide Retard Layer Pellets with and without a Swelling Layer In order to show the interaction of swelling layer and retard layer in the active substance release of the application according to the invention budesonide retard layer pellets with and without a swelling layer were prepared in accordance with the following composition:

| Composition [mg] | | |
| --- | --- | --- |
| | Amount per Dose of 9 mg Budesonide | |
| Component | Batch R020 | Batch R029 |
| 1. Active substance pellets | | |
| budesonide | 9.00 mg | 9.00 mg |
| lactose monohydrate | 36.00 mg | 36.00 mg |
| polyvinyl pyrrolidone (Kollidon K25) | 2.70 mg | 2.70 mg |
| polyoxyethylene(20) sorbitan mono-oleate (Polysorbate 80. Tween 80) | 0.71 mg | 0.71 mg |
| talcum | 16.50 mg | 16.50 mg |
| sugar-starch pellets | 260.00 mg | 260.00 mg |
| sum: | 324.91 mg | 324.91 mg |
| 2. Swelling layer pellets | | |
| carbomer | — | 24.00 mg |
| polyvinyl pyrrolidone (Kollidon K25) | — | 18.00 mg |
| talcum | — | 18.00 mg |
| sum: | 324.91 mg | 384.91 mg |
| 3. Retard layer pellets | | |
| Eudragit ® RS 12, 5 | 10.50 mg | 10.50 mg |
| Eudragit ® RL 12, 5 | 4.50 mg | 4.50 mg |
| triethyl citrate | 1.50 mg | 1.50 mg |
| talcum | 12.0 mg | 12.0 mg |
| sum: | 353.41 mg | 413.41 mg |

In view of the composition of the active substance and swelling layer batch R029 corresponds to the application according to the invention. However, compared to the application according to the invention coating of the retard layer intentionally was increased by a factor of 1.7. With said test batch it should be shown that the interaction or interplay, respectively of both layers in the context of the active substance release also works under extreme conditions and thus, a robust effect of the swelling layer exists. Batch R020 contained no swelling layer and served as a control batch. Except for said difference, control and test batch were composed identically. The pellets of both batches have not been coated with an enteric film. The parameters of the release test were as follows:

Release equipment: equipment 2 of the European Pharmacopoeia described in chapter 2.9.3 (stirrer blade method)
Volume of the release medium: 900 ml of artificial intestinal juice (i.e. no test on gastric juice resistance was performed)
Speed of rotation: 75 revolutions per minute
Temperature: 37.0° C.±0.5° C.
Test medium:
  Artificial intestinal juice (SGF): phosphate buffer ($KH_2PO_4$, NaCl, NaOH) with 0.1% of polysorbate, pH 6.5
Batches:
  Test batch: R029
  Control batch: R020
Number of test patterns: N=2
Sample pick and content
  determination: continuous with UV-on-line measurement (λ=255 nm)

Figure 5:
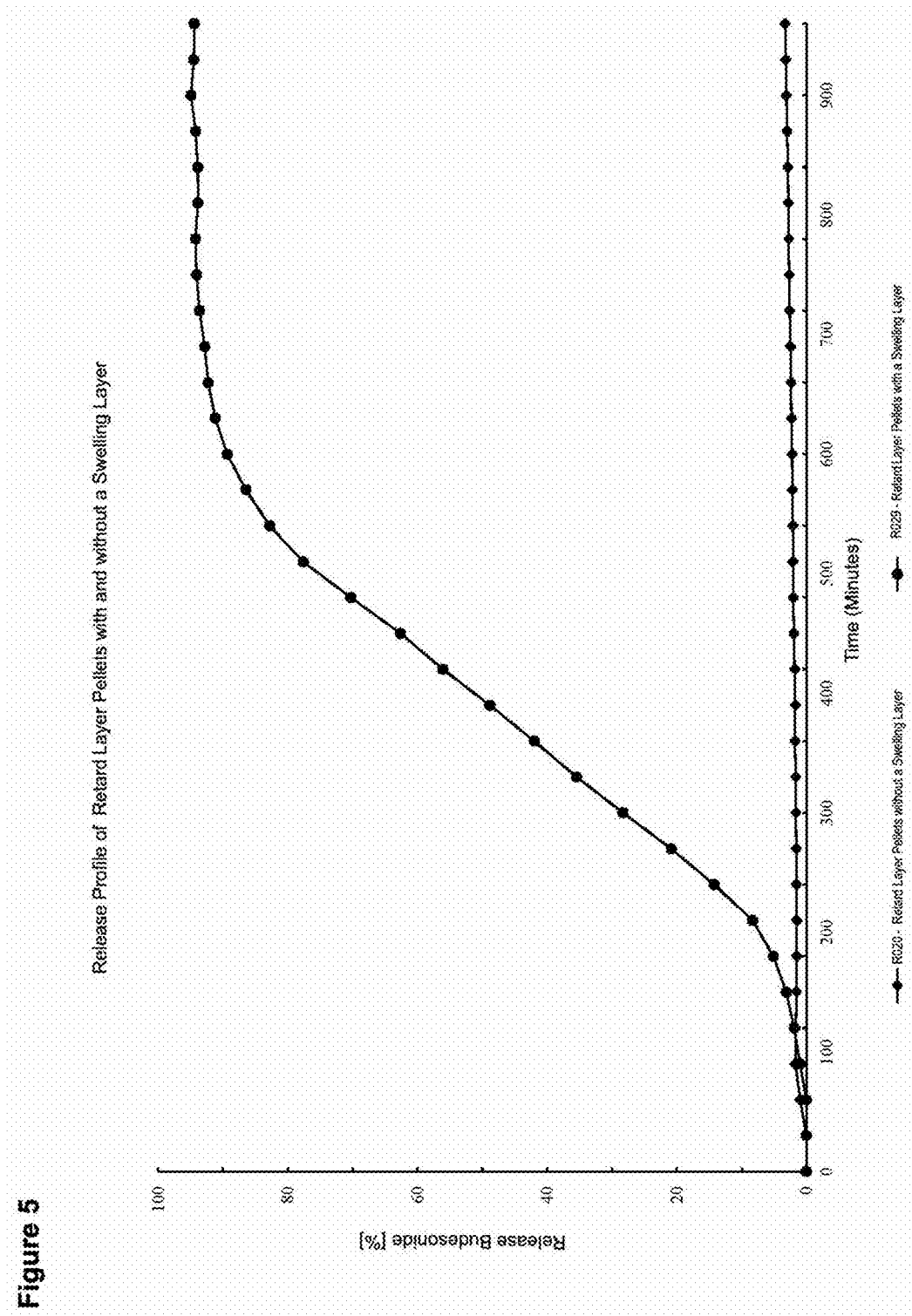
FIG. 5 shows the in vitro release profile of pellets according to the invention with and without swelling layer. The conditions of the trial are explained in detail in Example 2.

FIG. 5 shows the in vitro release profiles of the test and control batches. The effect of the swelling, layer is impressive and completely surprising. While no budesonide was released from the control batch over hours at all, the release profile of the test batch corresponds to the profile of the application according to the invention. Thus, only the simultaneous presence of the swelling and retard layers allows the desired delayed release of budesonide from the pellets. The retard layer alone in this regard is not functional. Thus, only the combination of the swelling and retard layers described for the application according to the invention is able to bring budesonide to its site of action, so that both layers together have to be considered as the active substance release controlling components of the formulation.

Example 3: In Vivo Pharmaco-Kinetics Profiles of the Budesonide Multilayer Pellets-Containing Capsule (Formulation According to the Invention) and of the Budesonide Capsule in the Prior Art/Reference In an open, randomized phase I study on the pharmaco-kinetics of the formulation according to the invention a single dose of the formulation according to the invention (BUX-PVII; 9 mg of budesonide) and of the budesonide capsule in the prior art (3×3 mg of budesonide as a single administration in the form of the reference pellets) were administered to 12 healthy male probands in fasting condition each. Essential pharmaco-kinetic parameters are illustrated in the following table 3.

TABLE 3

|  | Treatment with pellets according to the invention (BUX-PVII) | | Treatment with reference pellets (3 × 3 mg of budesonide) | |
| --- | --- | --- | --- | --- |
|  | $C_{max}$ (ng/mL) | $t_{max}$ (h) | $C_{max}$ (ng/mL) | $t_{max}$ (h) |
| N | 12 | 12 | 12 | 12 |
| Mean (SD) | 0.928 (0.755) | 7.75 (3.71) | 4.60 (4.85) | 5.26 (0.81) |
| Min | 0.193 | 2.00 | 1.04 | 4.50 |
| Max | 2.62 | 13.00 | 16.1 | 6.50 |

In table 3 N=number of probands; Mean (SD) means average value/standard deviation; Min=minimum value; Max=maximum value. In table 3, for $C_{max}$ and $t_{max}$ the respective mean of the maximum budesonide plasma levels of the single patients are illustrated independent of the measuring time.

Figure 6:
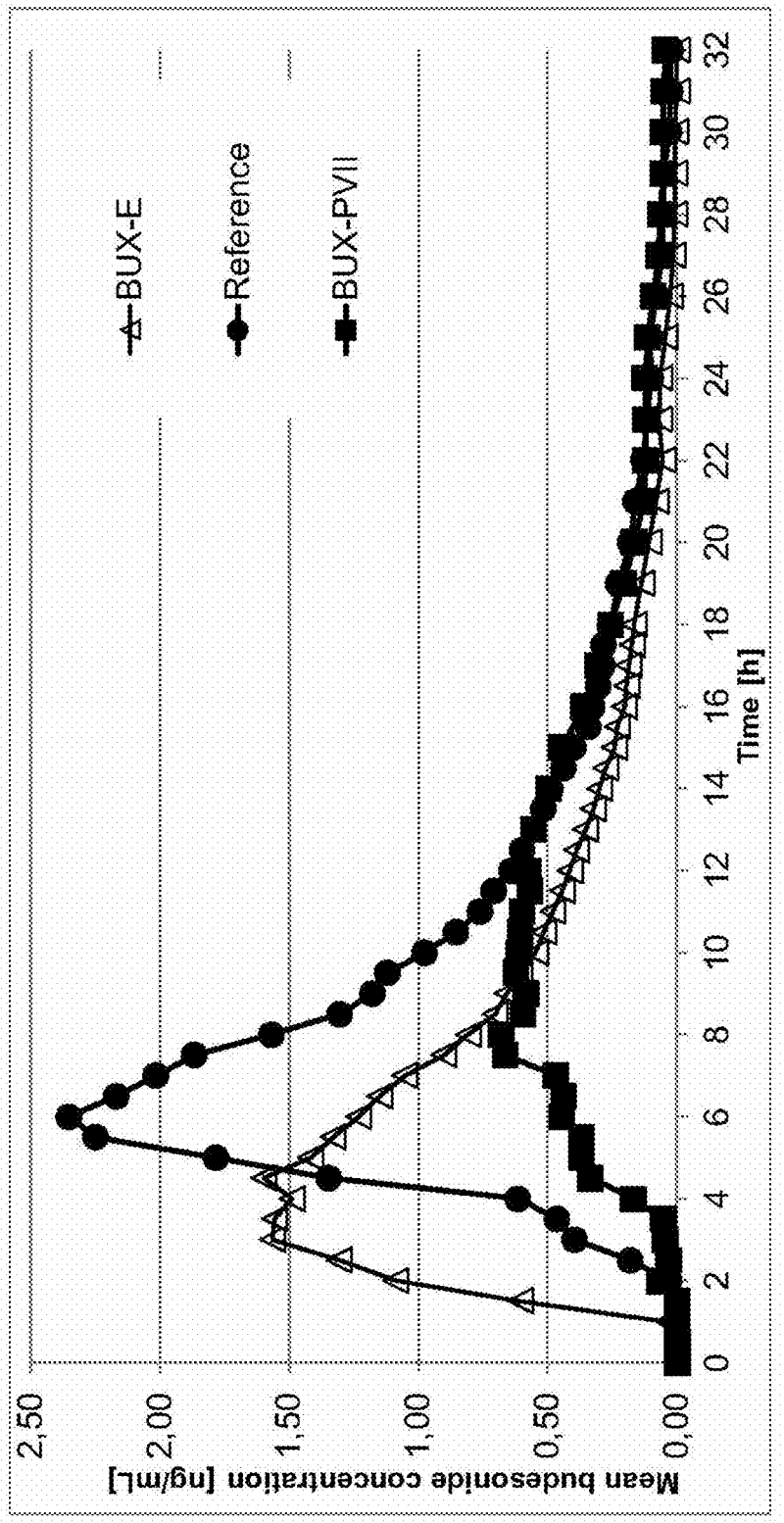
FIG. 6 shows the in vivo release characteristics obtained in open, randomized pharmaco-kinetics studies. Here, these are in vivo data, what explains possible differences to in vitro data.

The results of the in vivo pharmaco-kinetics study are graphically represented in FIG. 6. Compared to the values in table 3, in FIG. 6 the single values have been measured for the respective time point and the related mean has been calculated. Hence, the values of table 3 differ from the values of FIG. 6.

Example 4: In Vivo Pharmaco-Kinetics Profiles of the Budesonide Extrusion Pellets-Containing Capsule (Negative Example)

In an open, randomized phase I study on the pharmaco-kinetics of budesonide extrusion pellets a single dose of the budesonide extrusion pellets (9 mg in a gelatin capsule) as a single administration was administered to 16 healthy male probands in fasting condition each. Essential pharmaco-kinetic parameters are illustrated in the following table 4. Also, in table 4 the respective means of the maximum budesonide plasma levels of the individual patients are illustrated independent of the measuring time for $C_{max}$ and $t_{max}$.

TABLE 4

|  | Treatment with budesonide extrusion pellets (BUX-E) | |
| --- | --- | --- |
|  | $C_{max}$ (ng/mL) | $t_{max}$ (h) |
| N | 16 | 16 |
| Mean (SD) | 2.478 (0.9683) | 3.97 (1.407) |
| Min | 0.913 | 2.00 |
| Max | 3.95 | 7.00 |

Tables 3 and 4 confirm that the desired late release could only be achieved with the pellets according to the invention ($t_{max}$=7.75), whereas in the prior art $t_{max}$=5.26 and with the extrusion pellets $t_{max}$=3.97 was observed.

Example 5

Figure 2:
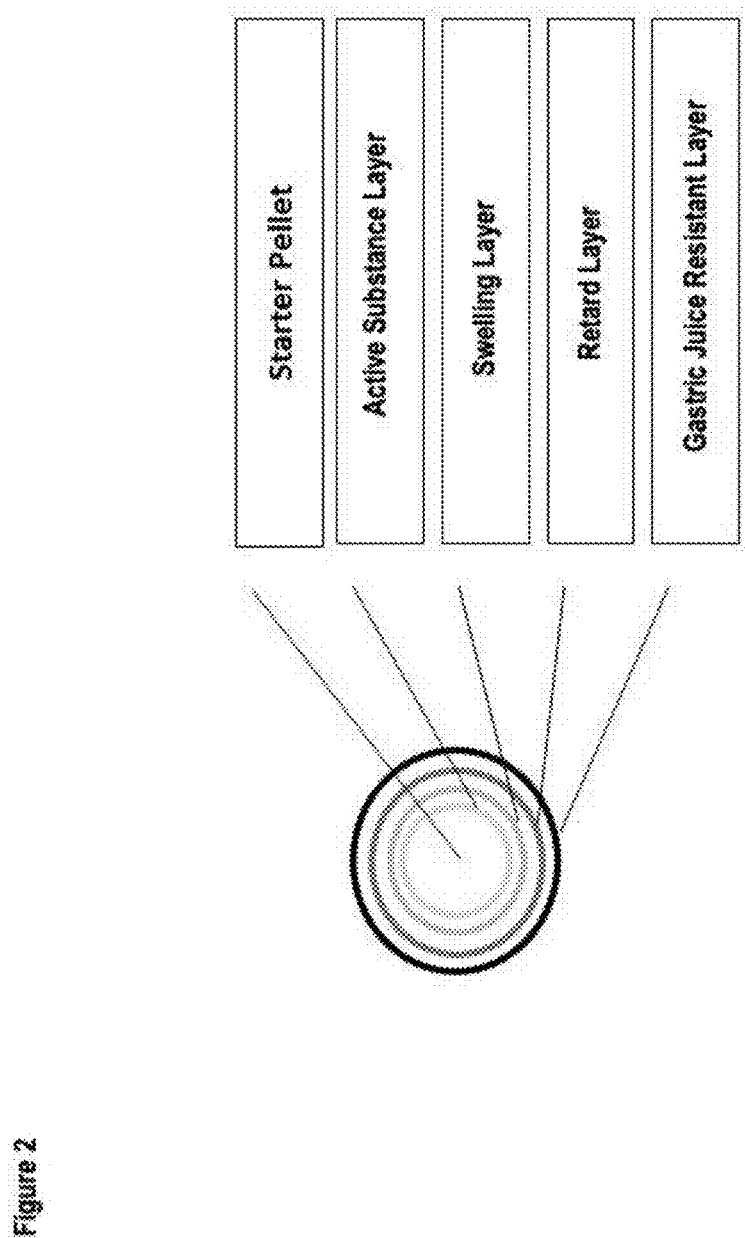
FIG. 2 schematically shows the structure of the pellets according to the invention for the delayed release of the active substance.

The results of this example are graphically illustrated in FIG. 6. FIG. 6 shows the budesonide plasma levels over time from the open, monocentric, randomized pharmaco-kinetics studies. Illustrated are the respective means of the budesonide plasma levels of all patients at the respective time of measurement. On the other hand, it is not relevant with the values of tables 3 and 4, respectively, when the respective patient showed the corresponding $C_{max}$ and $t_{max}$ value, respectively. In addition to the formulation according to the invention further prototypes of budesonide-containing drug formulations have been tested. The formulation designated BUX-PVII schematically illustrated in FIG. 2 allows an optimum colon targeting. The in vivo release profile to be achieved shall release the active substance—uniformly over a prolonged period with at the same time low serum plasma levels—after a delay phase. The mean plasma concentrations for budesonide after a single administration have been measured over time. In FIG. 6 there are plotted the results for two reference formulations (BUX-E and Reference) and for the formulation according to the invention (BUX-PVII).

Only the formulation according to the invention shows the desired release profile: a significant delay of the start of the release (ca. 3 hrs), plateau-like budesonide plasma levels over a prolonged period (over ca. 8 hrs), and in comparison, significantly lower budesonide plasma levels.

In this study, the profiles of the plasma concentrations over time for the drug formulation according to the invention were more homogeneous with less scattering between the individual participants of the clinical study.

Example 6

In an open clinical study over 8 weeks efficacy and tolerance of a prototype of the new oral 9 mg budesonide formulation have been investigated which was taken daily 1×. The aim of the study was to achieve a clinical remission, defined via an activity score of the disease of ≤4 (Colitis Activity Index, CAI), and via the CAI sub-scores 1 and 2 of 0 each. CAI sub-score 1 with a value of 0 describes a fecal frequency of less than 18 per week and CAI sub-score 2 with a value of 0 describes that no or at most 1 feces per week is allowed to be hematic. In this study, patients having an active ulcerative colitis were treated who could not successfully be treated with a mesalazine-containing preparation as a standard therapy. This pre-treatment had to be terminated before the start of the clinical study before the first intake of the study medication.

61 patients in total have been treated, 52 of whom have completed the study according to the protocol. The proportion of patients who achieved the aim of the study, the primary end point, is illustrated in table 5. In the so-called FAS group all the patients are summarized who have been treated with the test preparation at least 1×. In the so-called PP group those patients who have completed the study according to the protocol. In both analysis groups remission rates in this mesalazine-refractory study population of about 50% could be achieved.

TABLE 5

Analysis of the primary end point

| Analysis Group | Number (%) of patients in clinical remission type 1 at the end of the study | | | Clopper-Pearson 95% CI[1] |
|---|---|---|---|---|
| | N | n | % | |
| FAS | 61 | 29 | 47.5 | [34.60%, 60.73%] |
| PP | 52 | 28 | 53.8 | [39.47%, 67.77%] |

[1]CI, Confidence Interval (Full Analysis Set, FAS: Per Protocol Set, PP)

Figure 7:
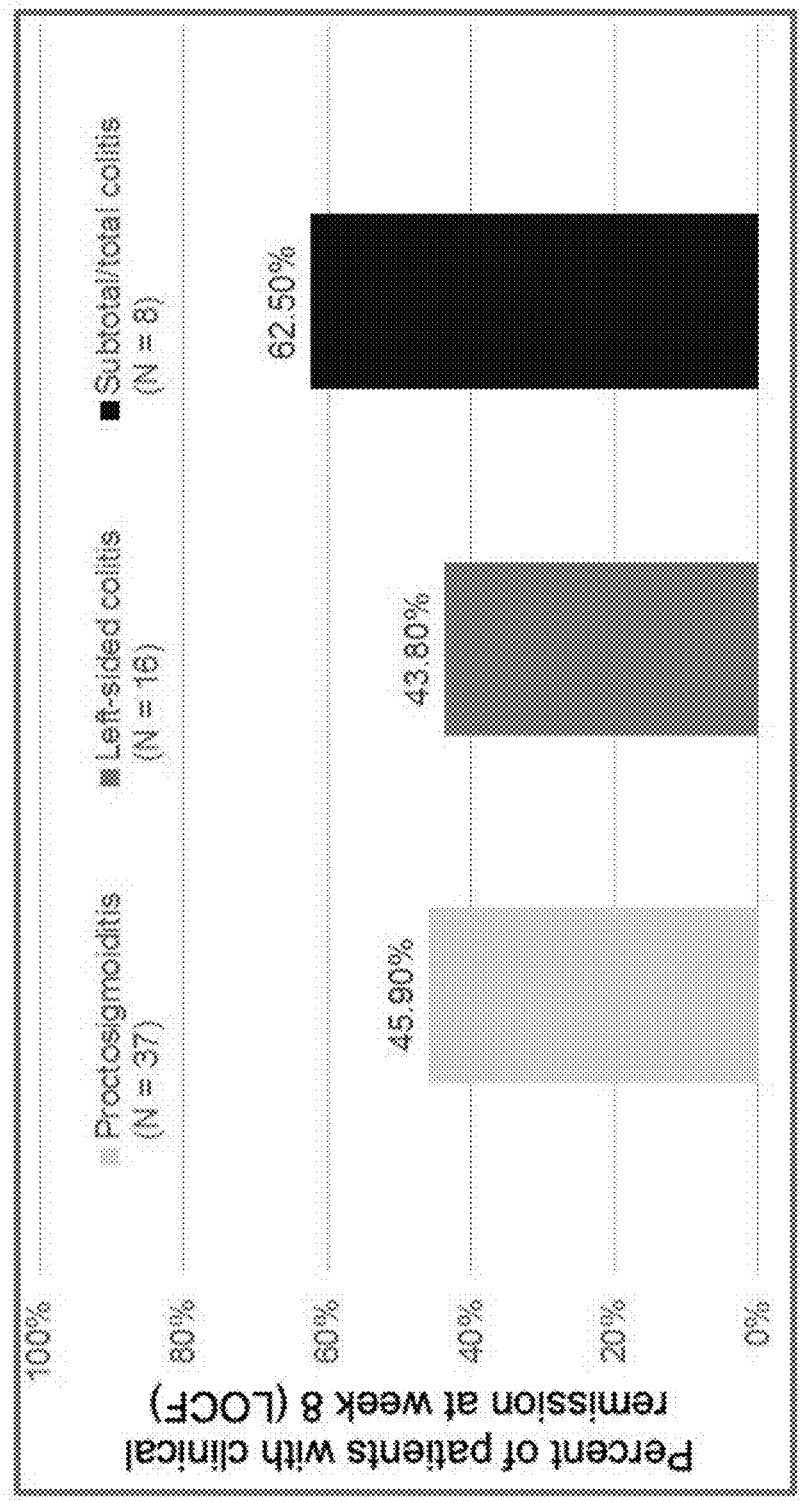
Figure 8:
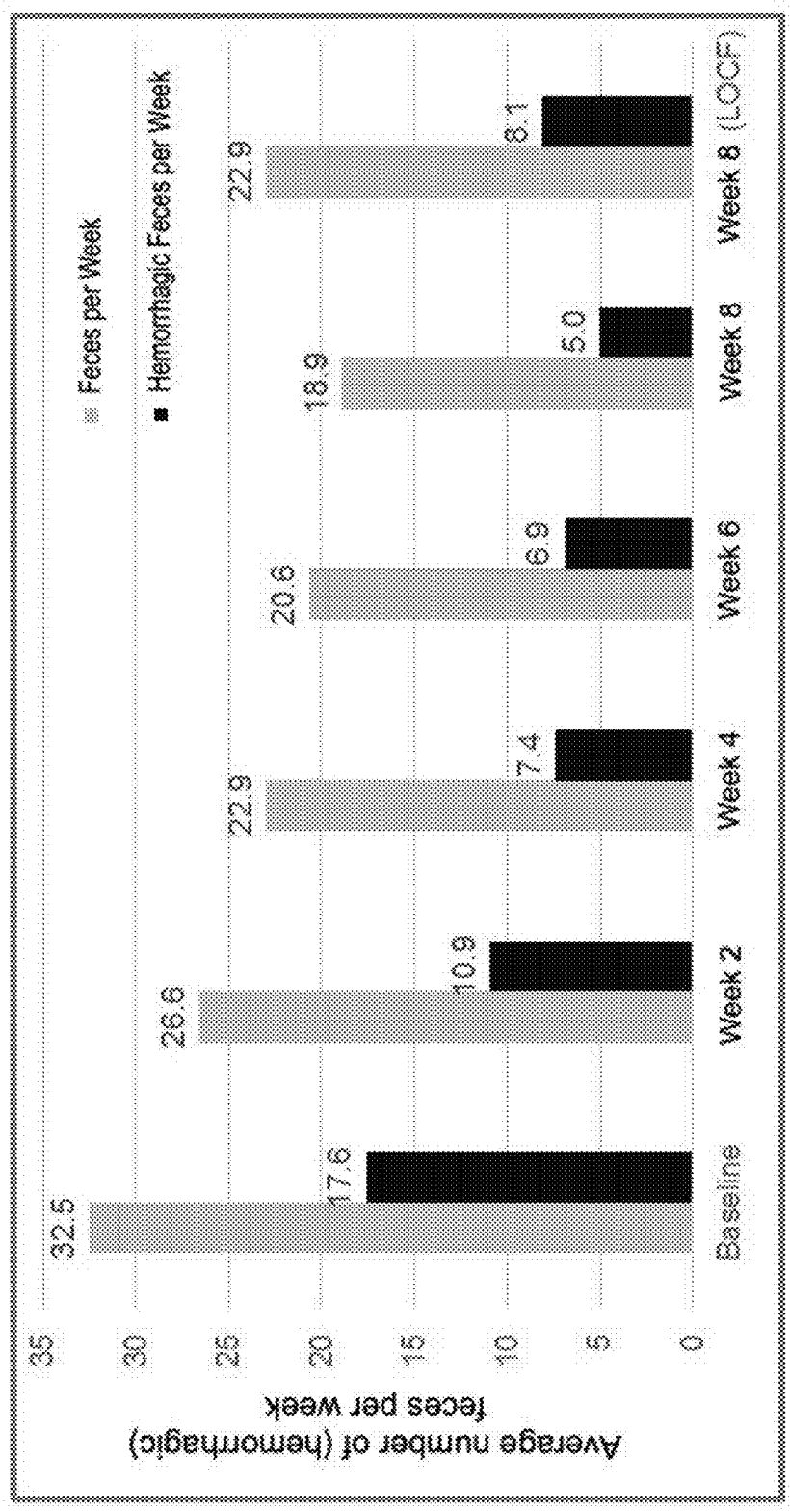
FIG. 8 shows the efficacy of the formulations according to the invention, as measured on the number of the hemorrhagic feces per week.

It could be shown in this study that the formulation according to the invention indeed effectively acts over the entire colon (FIG. 7). Consistent efficacy measured over the clinical remission rates does not show significant difference in the different segments of the colon. Also, the number of feces per week and number of hemorrhagic feces per week could effectively be decreased (FIG. 8). The formulation according to the invention could effectively and safe be used in this study. Safety of the application is confirmed by the measurement of morning cortisol. The measured average values remained within the normal range 6.2-18 g/dl.

The invention claimed is:

1. A pellet for the delayed release of an active substance in the distal colon having a multi-layer coating, wherein said pellet is composed of the following components:

a) a starter pellet consisting only of an inert material, further wherein said starter pellet contains no pharmaceutically active substance,
b) an active substance layer that is directly applied to said starter pellet a), further wherein said active substance layer contains both an active substance and film-forming excipients,
c) a swelling layer that is directly applied to said active substance layer b), further wherein said swelling layer contains swelling materials that swell upon contact with intestinal fluid,
d) a retard layer that is directly applied to said swelling layer c), further wherein said retard layer does not dissolve upon contact with intestinal fluid but rather becomes permeable for all fluids, and
e) an outermost coating that is directly applied to said retard layer d), further wherein said outermost coating does not dissolve at a pH value <5.5, but dissolves completely at a pH value greater than 6.0, wherein the active substance is budesonide or a pharmaceutically acceptable salt thereof.

2. A capsule rapidly soluble in the stomach, characterized in that said capsule is composed of a plurality of pellets according to claim 1.

3. The capsule according to claim 2, wherein each of said plurality of pellets comprises a powder particle having a spherical shape of uniform surface condition and an average diameter of 0.2 to 2.0 mm, further wherein at least 90% of the said powder particles contained with said capsule lie within the given size range.

4. The capsule according to claim 3, wherein at least 95% of said powder particles contained with said capsule have a size distribution lying with the range between 0.2 and 2.0 mm.

5. The pellet according to claim 1, characterized in that said active substance layer b) contains, in addition to the active substance budesonide or pharmaceutically acceptable salt thereof, a filler, a binder, a wetting agent and a separator.

6. The pellet according to claim 1, characterized in that the active substance is budesonide or pharmaceutically acceptable salt thereof in the form of micronized particles, further wherein 100% of said micronized budesonide particles are smaller than 10 μm and at least 95% of the micronized budesonide particles are smaller than 5 μm.

7. The pellet according to claim 1, characterized in that said swelling layer c) contains homo-polymeric polyacrylic acid of the A type as swelling agent in combination with a binder and a separator.

8. The pellet according to claim 1, characterized in that said retard layer d) is composed of a combination of ammonium methacrylate copolymer (type A) and ammonium methacrylate copolymer (type B).

9. The pellet according to claim 1, characterized in that said outermost coating e) does not dissolve at a pH value below 6.0 and is composed of a poly(meth)acrylic acid/poly (meth)acrylate copolymer with a ratio of poly(meth)acrylic acid to polymethylmethacrylate of 1:1.

10. The pellet according to claim 1, characterized in that, with an in vitro release in artificial gastric juice with a pH value of 1.2 for up to 2 hours, there is substantially no release of budesonide whereas in artificial intestinal juice at the pH of 6.5, after 270 minutes 10 to 30%, after 330 minutes 40 to 70%, and after 540 minutes more than 80% of said active substance budesonide is released.

11. The pellet according to claim 1, characterized in that, in accordance with test conditions of a pharmaco-kinetics study, less than 30% of the active substance is released in vivo within four hours.

12. The pellet according to claim 1, characterized in that, in accordance with test conditions of a pharmaco-kinetics study, the maximum plasma concentration in the mean is only achieved in vivo after 7.0 to 7.5 hours at the earliest.

13. The capsule according to claim 2, further wherein said capsule is a gelatin capsule that is easily dissolved in the stomach.

14. The capsule according to claim 13, characterized in that said capsule contains 3 mg to 9 mg of budesonide.

15. A sachet containing pellets according to claim 1 in such an amount that one sachet contains between 3 mg and 9 mg of budesonide.

\* \* \* \* \*